United States Patent [19]

Lancellotti

[11] 4,218,215

[45] Aug. 19, 1980

[54] AMALGAM CARRIER AND CONDENSER

[76] Inventor: Joseph J. Lancellotti, 8 Starr Rd., East Brunswick, N.J. 08816

[21] Appl. No.: 969,475

[22] Filed: Dec. 14, 1978

[51] Int. Cl.³ .................................................. A61C 5/04
[52] U.S. Cl. ...................................................... 433/90
[58] Field of Search .................. 32/60, 51, 52; 433/90

[56] References Cited

U.S. PATENT DOCUMENTS

| | | | |
|---|---|---|---|
| 608,984 | 8/1898 | Hanson | 32/51 |
| 1,797,866 | 3/1931 | Ivory | 32/60 |
| 2,352,808 | 7/1944 | Siqveland | 32/60 |
| 2,476,793 | 7/1949 | Arena | 32/51 |
| 2,679,102 | 5/1954 | Ivory, Jr. | 32/60 |
| 2,696,670 | 12/1954 | Thurman | 32/60 |
| 3,221,409 | 12/1965 | Thiel et al. | 32/60 |
| 3,735,492 | 5/1973 | Karter et al. | 32/60 |
| 4,079,518 | 3/1978 | Marshall | 32/60 |

Primary Examiner—Louis G. Mancene
Assistant Examiner—John J. Wilson
Attorney, Agent, or Firm—Arthur L. Plevy

[57] ABSTRACT

A combination amalgam condenser and carrier apparatus employs a base assembly which accommodates a rod. The rod is employed in both a carrier and a condenser position and is located within a plunger member and retained therein by means of a securing member which is positioned between two prongs formed at the end of a lever member. The lever member is pivotally mounted with respect to the handle and by moving the lever, one can operate the apparatus in a condenser position where the rod protrudes from the plunger and in a carrier position where the rod is located within the plunger. The lever member has a clip mechanism which coacts with a latch mechanism located on a carrier base assembly; which base assembly is integrally formed with the rod. The clip mechanism as coacting with the latch provides a locking action defining a condenser position when the lever is pivoted towards the handle. When the locking mechanism is released, the apparatus is operative in a carrier position as defined by the rod located within the plunger.

9 Claims, 16 Drawing Figures

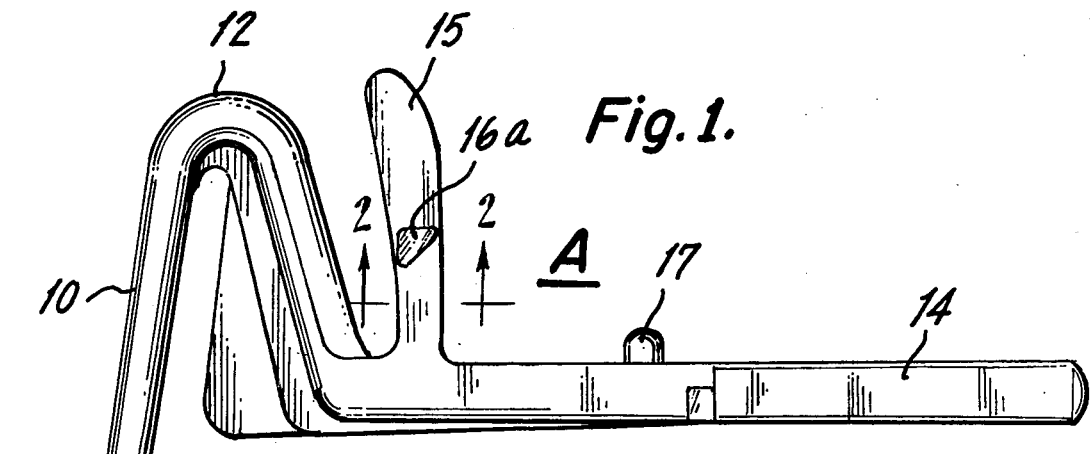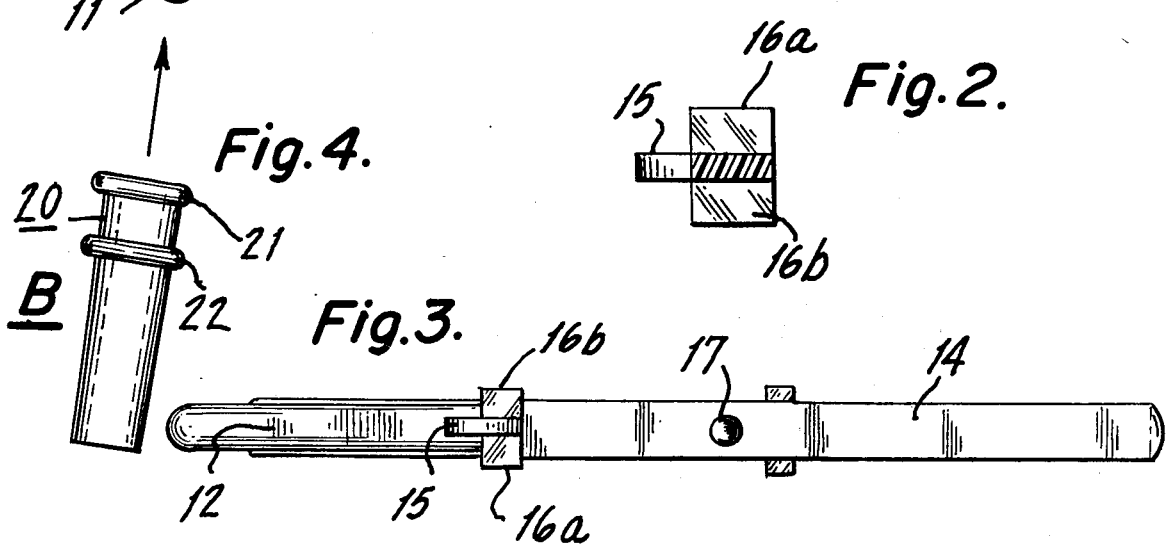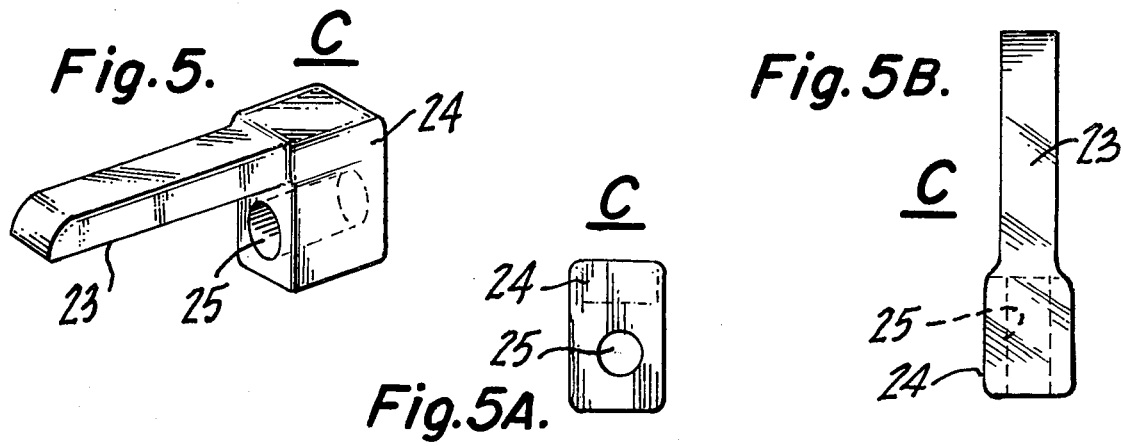

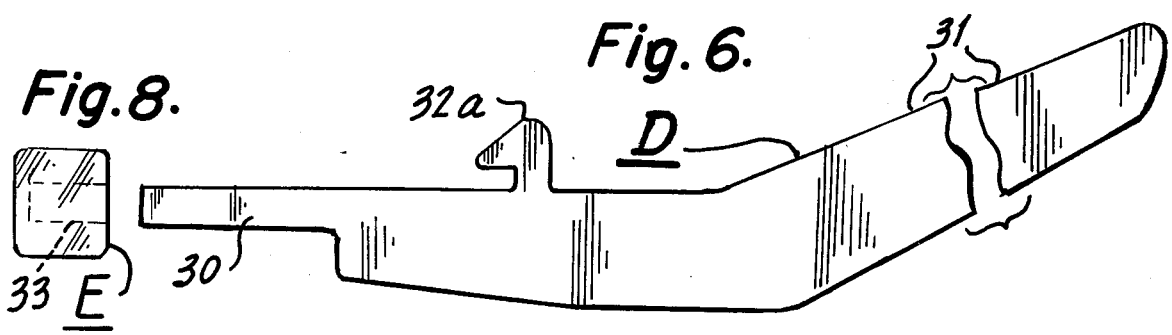
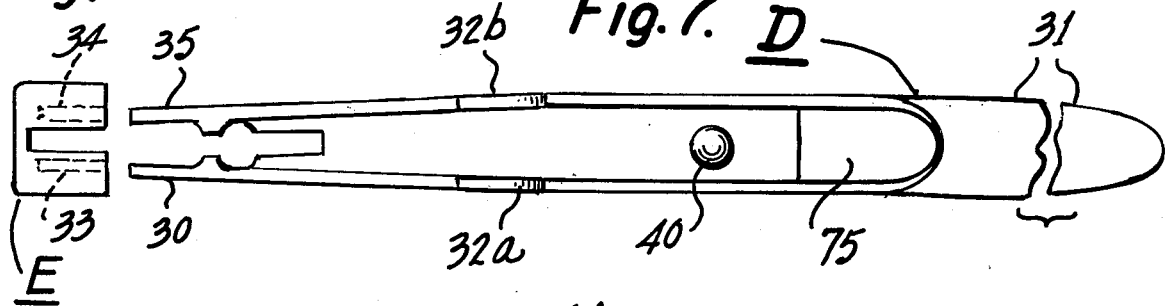
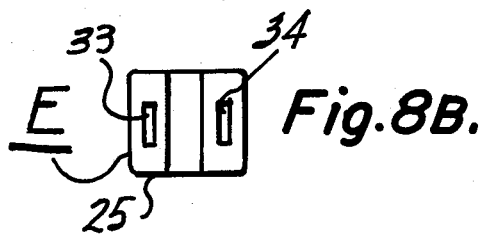
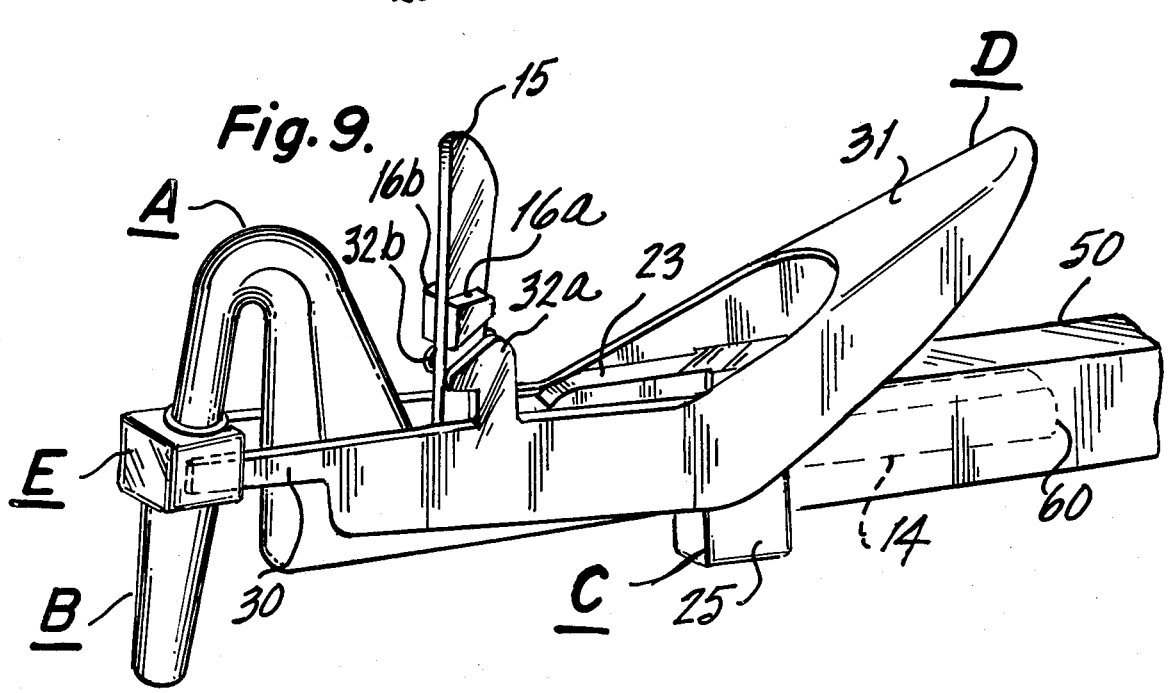

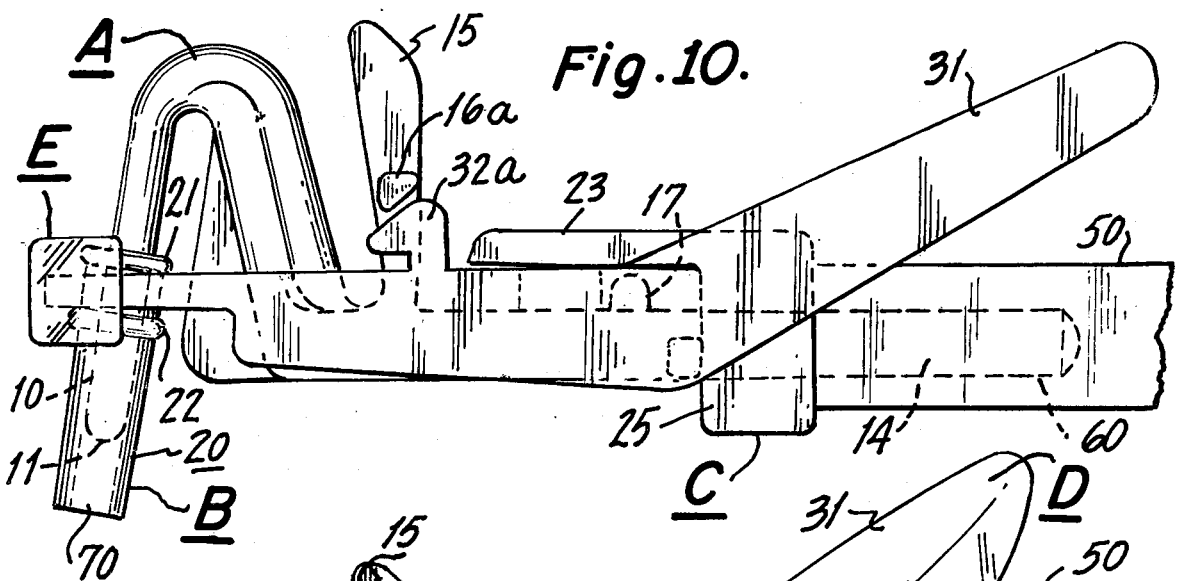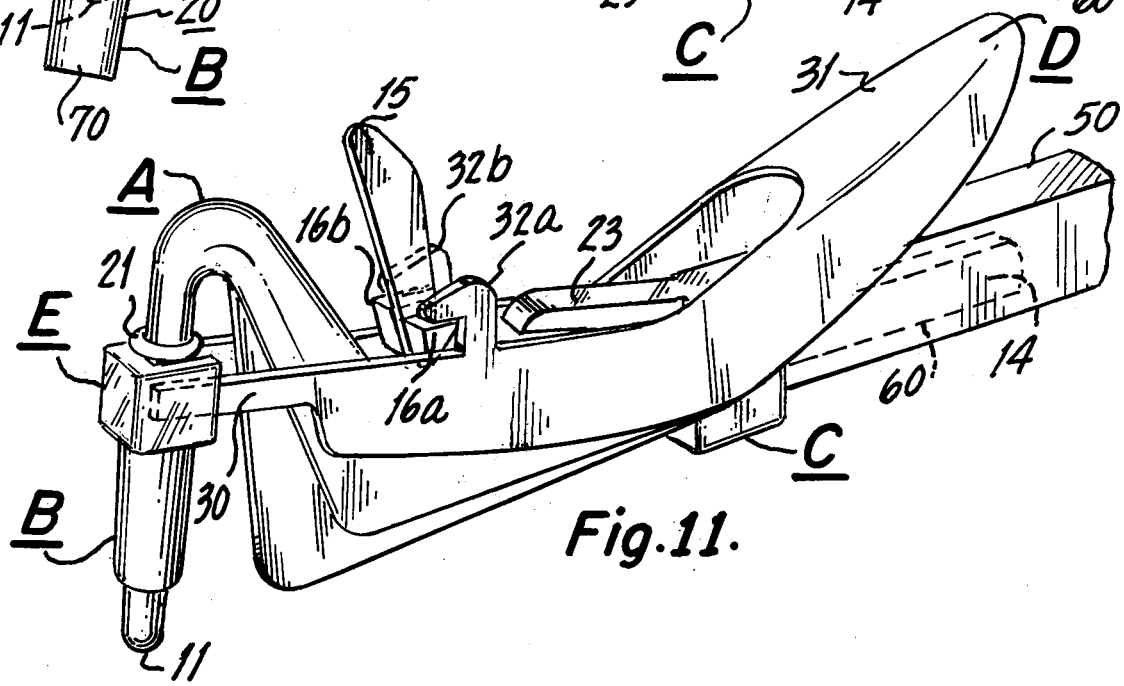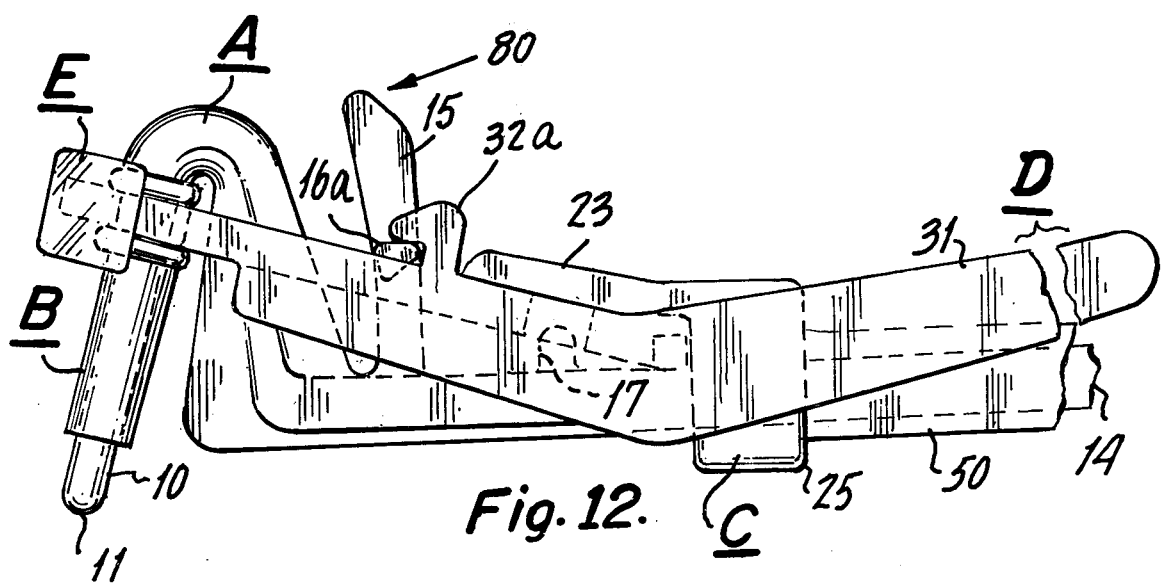

4,218,215

AMALGAM CARRIER AND CONDENSER

BACKGROUND OF INVENTION

This invention relates to a combination of an amalgam carrier and condenser and particularly relates to apparatus which performs an amalgam carrying and condensing operation within a single unique structure.

There presently exists many amalgam carriers which are lever activated and so on. Generally, an amalgam carrier is a device which is adapted for picking pieces of amalgam and transferring them to cavities in the teeth of a patient. The transported amalgam is then condensed within the cavity by means of a separate instrument commonly referred to as a condenser.

Thus, in many prior art applications, the practitioner is required to utilize both a carrier instrument and a condenser instrument in order to fill a patient's cavity with amalgam. The prior art, being cognizant of such problems, has offered instruments which function both as a carrier and a condenser to attempt to incorporate both functions in a single instrument.

Examples of such combinations can be had by referring to prior United States patents such as U.S. Pat. No. 2,696,670 entitled Combination Amalgam Carrier and Plugger by Robert B. Thurman issued on Dec. 14, 1954. This instrument provides a locking means which enables one to lock a slideable piston in a condenser position. The lock provided affords a twisting operation wherein a plugger handle is twisted into a slot formed in the housing.

Other patents such as U.S. Pat. No. 2,917,830 employ a rotatable mechanism which enables one to rotate the device to enable operation of the same in a condenser position. Still other patents as U.S. Pat. No. 3,221,409 incorporate a separate dispensing mechanism located adjacent the carrier portion to enable the practitioner to carry and dispense amalgam. Similar apparatus is shown in U.S. Pat. No. 2,476,793 entitled Amalgam Carrier Condenser Attachment.

Other patents such as U.S. Pat. No. 1,797,866 and 3,735,492 show various alternate embodiments for providing carrying or condenser operations.

Basically, a review of the prior art as indicated above shows that such devices are extremely complicated and have severe limitations in their operating characteristics. There are certain problems which are typical in regard to such devices. In many instances, the plugger which is associated with the carrier becomes coated with silver or amalgam which jams the instrument and in essence, locks the carrier rod to the plugger. This renders the instrument unusable.

In certain other instruments, the combination of the condenser and the carrier render the instrument extremely difficult to use as the practitioner has to rotate the instrument and so on. Essentially, many of the instruments described in the prior art are extremely difficult to manufacture based on the fact that they are complicated and difficult to implement and to build.

It is therefore an object of the present invention to provide a lever type amalgam carrier and condenser apparatus which is simple to use, easy to operate, and inexpensive to manufacture. The apparatus thus provided further enables one to rapidly gain access to the plunger and rod apparatus to enable rapid cleaning or replacement, as desired.

The combination further provides an effective locking means whereby activation of the locking means enables the practitioner to use the tip of the plugger rod as a condenser in a first lock position and to use the apparatus in a second unlocked position in an amalgam carrying operation.

BRIEF DESCRIPTION OF PREFERRED EMBODIMENT

A dental amalgam carrier, condenser apparatus comprises a rod carrying base member having a front section defining a rod with an arcuate central section coupled to a relatively cylindrical rear section, said base member including a transverse latching member extending therefrom and a lever member pivotally mounted with respect to said base member, said lever member including a clip mechanism which moves as said lower member is pivoted and positioned to coact with said latching member in a first position to lock said lever member with respect to said base member in said first position and a plunger member coupled to said lever member and having a central aperture, with said rod of said base member located therein, said plunger adapted to move as said lever member moves and to lock when said lever member is in said first position to cause said rod to extend from said plunger member defining a condenser position, and to cause said rod to be within said plunger when said lever member is in a second position different than said first to define a carrier position whereby amalgam can be carried by said plunger when said rod is within said plunger and discharged when said plunger is moved to said first position by said lever member.

BRIEF DESCRIPTION OF THE FIGURES

FIG. 1 is a side view of an amalgam base assembly according to this invention.

FIG. 2 is a sectional view taken through line 2—2 of FIG. 1.

FIG. 3 is a top plan view of the base assembly of FIG. 1.

FIG. 4 is a perspective plan view of a plunger assembly.

FIG. 5 is a side view of a locking assembly.

FIG. 5A is a front view of a locking assembly; while FIG. 5B is a top view of the locking assembly.

FIG. 6 is a side view of a lever assembly.

FIG. 7 is a top plan view of the lever assembly of FIG. 6.

FIG. 8 is a side view of a securing member.

FIG. 8A is a top view of the securing member of FIG. 8; while

FIG. 8B is a front view of the securing member.

FIG. 9 is a perspective view of the assembled apparatus in a carrier position.

FIG. 10 is a side view of the apparatus of FIG. 9 in a carrier position.

FIG. 11 is a perspective view of the apparatus in a condenser position.

FIG. 12 is a side view of the apparatus of FIG. 11.

DETAILED DESCRIPTION OF THE INVENTION

Before proceeding with a detailed description of the FIGS., a brief explanation of how the invention is going to be described will be afforded.

Essentially, the combination instrument consists of a number of parts, all of which are fitted together to perform an amalgam carrier and condenser operation.

The fabrication of the parts in the manner described enables operation of the device in a carrier and a condenser mode. A description will first be made of each individual component and then this will be followed by a showing or description of the apparatus in the representative modes showing all the individual components completely assembled as on the final instrument to enable one to gain a clear insight to the operation of the device.

Referring to FIG. 1, there is shown an arcuate amalgam carrier base member A. Essentially, the base member A contains an amalgam carrier rod 10 at a first end. The rod 10 has a rounded bottom surface 11. The rod 10 is integrally formed with the base member A and continues upwards in a first arcuate curve 12 and thence, downwardly unto a relatively long base member portion 14.

Extending from the base member portion 14 is a relatively transverse latch member 15. The latching member 15 contains a projection 16a which is relatively perpendicular to member 15. There is another member 16b located on the opposite end of the latch member 15 as shown in FIG. 2 which is a section taken through line 2—2 of FIG. 1.

Also shown located on the surface of the base member 14 is a circular projection 17 which, as will be explained, serves to coact with an aperture formed in a lever member D to be described.

FIG. 3 shows a top view of the member of FIG. 1 employing the same reference numerals to enable one to gain a clearer insight to the nature and construction of the base member assembly A. Essentially, the member A may be fabricated from plastic and molded as an integral piece as shown. The base member A comprises a first part of the apparatus to be described.

Shown in FIG. 4 and located beneath the rod 10 is a cylindrical plunger member B. The plunger 20 has a centrally extending aperture which is of a greater diameter than the rod 10 and enables the rod to be inserted within the plunger B. The plunger B has a top flange 21 and a lower flange 22. Interdisposed between the two flanges 21 and 22 will be two prongs associated with a lever member D to be described.

Referring to FIG. 5, there is shown a locking member C. The locking member C is essentially an L-shaped member having an extending front portion or arm 23 and a rear portion 24 which is perpendicular to the arm portion 23. The rear portion has an aperture 25 located therein; which aperture is of a suitable diameter to enable insertion of the rear portion 14 of the base member A into the aperture.

Referring to FIG. 6, there is shown a lever member D. The lever member D has a front end 30 which is a pronged or forked arrangement and as will be shown, is positioned between the flanges 21 and 22 of the plunger member B. The lever member D is basically a rocker arm and has a relatively long inclined end 31 which enables one to pivot or rock the lever member to actuate or move the plunger member B with respect to the rod 10 of the member A.

Extending and coupled to the lever member D is a locking clip 32a. The clip 32a is located on one side of the member D, while another clip 32b (FIG. 7) is located on the other side. As will be explained, when the lever member is actuated, the clips 32a and 32b coact with the projections 16a and 16b on the base member A and lock the lever and hence, the rod in a condenser position.

Shown adjacent the lever member D is a securing member E (FIG. 8). Securing member E is of a "U" shaped configuration as shown in the top view of FIG. 8A and has two apertures as 33 and 34 which enable the securing member to be inserted into the forked projections as 30 and 35 of the lever member D as depicted in views of FIG. 7 and FIG. 8A. A front view of the securing member E is shown in FIG. 8B.

Referring to the top view of the lever member D, there is shown an aperture 40 which coacts with the projections 17 in the base member A when the unit is assembled, as will be explained.

Thus, as one can ascertain, the apparatus to be described consists essentially of the following main parts:

The base assembly member A which contains the carrier rod 10;

The plunger member B;

The locking member C;

The lever member D; and

The securing member E.

Referring to FIG. 9, there is shown a perspective view of the apparatus in an assembled position. FIG. 9 depicts a further member 50 which is a handle member. The member 50 has an aperture at one end which enables insertion of the rear portion 14 of member A into the aperture. The handle member 50 may be of a convenient desired length to enable the practitioner to optimimly use the device. The position shown in FIG. 9 is the carrier position as one can ascertain, and the clip 32a is located beneath projection 16a as can be seen.

Referring to FIG. 10, there is shown a side view of the mechanism depicted in FIG. 9. Essentially, in FIG. 10, the component parts are positioned as follows:

The base member A has its rear portion 14 inserted into the apreture 60 of the handle 50. The lever member D is positioned above the base member A with its forked ends 30 and 35 located between the space of plunger B as provided between flanges 21 and 22. The securing member E is positioned or clipped between the flanges and secures the plunger about the rod 10 by coacting with the extended forked ends 30 and 35 of lever D. The aperture of lever D is seated within the projection 17 of member A. The locking member C has its arm 23 positioned above the lever member D with the aperture 25 located about the rear portion 14 of the base assembly A.

Hence, it can be seen from FIG. 10 that the plunger member B can be removed easily and rapidly by removal of member E and hence, one can clean the rod 10 or plunger member B as desired. It is further noted that one can remove the assembled pieces A through E from the handle 50 by merely removing the rear portion 14 of member A from the aperture 60. One can then remove the locking member C to thereby release and remove the additional members.

The unit as shown in FIGS. 9 and 10 is in a carrier position and as such, the rod 10 is positioned within the plunger B. There is an area 70 formed between the end 11 of the rod 10 and the tip of the plunger member B. Thus, the practitioner can insert the tip end of the plunger into a source of amalgam. The amalgam is carried within the aperture 70 and can be directed by the practitioner to the tooth or cavity of the patient.

Referring to FIGS. 11 and 12, there is shown the apparatus in a condenser position. In this position, the lever D has been pivoted towards the handle 50. The clip sections 32a and 32b are now located above the projections 16a and 16b associated with the latch member 15.

As can be seen from the FIGS., the bottom edge of the clip 32a is now located on the top surface of the member 16a. A similar action occurs for clip 32a and projection 16b. Accordingly, the assembly is now in a locked position with the rod 10 protruding from the plunger B. The rounded end 11 of the rod 10 can now be used by the practitioner to form the amalgam in the patient's tooth.

It is noted also that as the lever D is moved from the carrier position as shown in FIGS. 9 and 10 to the condenser position as shown in FIGS. 11 and 12, that the amalgam contained in the area 70 is discharged as the rod moves from the position shown in FIG. 10 to the position shown in FIG. 11.

Once the apparatus is in the position depicted in FIGS. 11 and 12, the rod 10 is locked and the practitioner can now selectively distribute the amalgam as desired by using the rod 10 as a condenser mechanism. When more amalgam is required, the user merely pushes the member 15 in the direction of the arrow 80 and hence, releases the clips 32a from the projections 16a and 16b and thus unlocks the mechanism. Hence, as can be seen the apparatus is now in the carrier position as indicated in FIGS. 9 and 10 and hence, the apparatus is adapted to again receive amalgam.

As is seen in FIGS. 11 and 12, when the lever member D is in the position shown the locking member C acts as a spring. The arm 23 is distorted or flexed upwardly during pivoting of the lever D and tends to push the lever downwardly. Hence, the member C serves to force the lever clip 32a unto the top of the projection 16a to assure reliable locking. When member 15 is moved (arrow 80), the member C forces the lever back to the carrier position as depicted in FIGS. 9 and 10. It is, of course, seen that the arm 23 of the locking member C is inserted through the aperture 75 (FIG. 7) of the lever member D and hence, secures the lever member D as further aided by aperture 40 which coacts with the projection 17 on base member A.

It is thus shown that there is provided a combination condenser and carrier apparatus which is simple to use and extremely economical to manufacture as all parts as depicted above can be molded from a suitable plastic or other material. The instrument shown provides rapid operation between the carrier and condenser position, while it is simple to maintain and clean based on the construction afforded.

It is, of course, apparent that the various shapes and parts as depicted are by way of example and many alternatives will be apparent to those skilled in the art and which are deemed to be encompassed within the spirit and scope of this invention.

I claim:

1. A dental amalgam carrier, condenser apparatus, comprising:
   (a) a rod carrying base member having a front section defining a rod with an arcuate central section coupled to a relatively cylindrical rear section, said base member including a transverse latching member extending therefrom, said transverse latching member comprising a planar member having a projection located on one side thereof, with said projection extending from said side and relatively transverse to said planar member,
   (b) a lever member pivotally mounted with respect to said base member, said lever member including a clip mechanism which moves as said lever member is pivoted and positioned to coact with said latching member in a first position to lock said lever member with respect to said base member in said first position, said clip mechanism having a front section adapted to coact with said projection in said first position to cause said front section to latch upon the surface of said projection,
   (c) a plunger member coupled to said lever member and having a central aperture, with said rod of said base member located therein, said plunger adapted to move as said lever member moves and to lock when said lever member in said first position to cause said rod to extend from said plunger member defining a condenser position, and to cause said rod to be within said plunger when said lever member is in a second position different than said first to define a carrier position whereby amalgam can be carried by said plunger when said rod is within said plunger and discharged when said plunger is moved to said first position by said lever member.

2. The dental apparatus according to claim 1 further including:
   handle means of a cylindrical configuration and having a front aperture for insertion therein of said cylindrical rear portion of said base member.

3. The apparatus according to claim 1 wherein said latching member is relatively flexible to enable movement of the same in an amount sufficient to free said clip from said projection.

4. The dental apparatus according to claim 1 wherein said lever member has a front forked section adapted to surround said plunger to allow said plunger to move as said lever moves, and a selectively removable securing member coupled to said forked section to retain said plunger about said front section rod of said base member.

5. The apparatus according to claim 4 wherein said plunger member has a first and second flange located on the outer surface thereof at a predetermined separation with said forked section of said lever member positioned between said flanges to enable said lever to move said plunger by said forked section coacting with one of said flanges.

6. The dental apparatus according to claim 1 further including locking means coupled to said base member and positioned above said lever member, said locking means coacting with said lever member in said first position to urge said lever member and therefore said clip unto said projection.

7. The apparatus according to claim 1 wherein said transverse latching member has a first projection on a first side and a second projection on a second side, said projections extending from said latching member and relatively transverse thereto, and a first and a second clip member coupled to said lever member at first and second sides and each adapted to coact with one of said projections when said lever is moved to said first position.

8. The apparatus according to claim 1 wherein said plunger is adapted to move a predetermined distance between said first position, wherein said rod extends from said plunger and a second extreme position wherein said rod is within said plunger to form an area between the tip of said rod and the end of said plunger capable of accommodating a given amount of amalgam.

9. The dental amalgam carrier condenser apparatus according to claim 1 wherein said rod base member, said lever member, and said plunger member are fabricated from a plastic.

* * * * *